United States Patent [19]

Huynh-Dinh et al.

[11] Patent Number: 4,842,996

[45] Date of Patent: Jun. 27, 1989

[54] PROBES COMPRISING MODIFIED ADENINE GROUPS, THEIR PREPARATION AND THEIR USES

[75] Inventors: Tam Huynh-Dinh, Croissy sur Seine; Jean Igolen, Le Mesnil St Denis, both of France

[73] Assignees: Institut Pasteur; Centre National de la Recherche Scientifique, both of Paris, France

[21] Appl. No.: 768,042

[22] Filed: Aug. 22, 1985

[30] Foreign Application Priority Data

Aug. 22, 1984 [FR] France ............................ 84 13095

[51] Int. Cl.$^4$ ............................................. C12Q 1/68
[52] U.S. Cl. ........................................ 435/6; 536/26; 536/27; 935/77; 935/78
[58] Field of Search ............... 536/27, 26; 435/6; 935/77, 78

[56] References Cited

U.S. PATENT DOCUMENTS 4,556,643  12/1985  Paau ........................................ 435/6
4,563,417  1/1986  Albanella ............................... 435/6

OTHER PUBLICATIONS

Chemical Abstracts, vol. 94, No. 13, p. 232, No. 97632j (Mar. 30, 1981).
Kirnos, Chemical Abstracts, 88:101277t.
Gaffney—I, Nucleic Acids Research, 10(4), pp. 4351–4361 (1982).
Gaffney—II, Tetrahedron, 40(1), pp. 3–13 (1984).

*Primary Examiner*—Esther M. Kepplinger
*Assistant Examiner*—Robert Benson
*Attorney, Agent, or Firm*—Finnegan, Henderson, Farabow, Garrett and Dunner

[57] ABSTRACT

The invention relates to a probe constituted by an oligonucleotide fragment of structure predetermined by the application envisaged, wherein at least a part of the adenine groups therein is replaced by modified adenine groups so that they can form three hydrogen bonds with the reactive groups of thymine or uracil. This probe is useful in the field of biological analyses and extractions.

14 Claims, No Drawings

PROBES COMPRISING MODIFIED ADENINE GROUPS, THEIR PREPARATION AND THEIR USES

BACKGROUND OF THE INVENTION

The invention relates to probes constituted by polynucleotides, more precisely oligonucleotide fragments, comprising, as purine bases, adenine groups modified so that they are capable of forming three hydrogen linkages with reactive groups of thymine, a process for their production, as well as their uses.

It is now well known to specialists to use for certain analyses techniques based on hybridization between a predetermined sequence of nucleotides used as a probe and a nucleotide sequence complementary to those of the probe. These techniques are especially useful for the detection of particular nucleotide sequences, such as DNA or RNA sequences and the isolation of such sequences. The nucleic acid sequence may possibly be contained in a composition containing nucleic acids. The practice of these techniques, in particular the obtaining of probes that are sensitive and capable of hybridizing stably with the complementary sequences, still poses problems.

Thus, one of the most frequent problems posed in genetic engineering is that of "fishing" for RNA messengers by synthetic oligodesoxynucleotides, that is to say the detection, isolation and analysis of messenger RNA sequences by hybridization with complementary DNA fragments (cDNA). This technique is based on the matching of A-T pairs (2 hydrogen bonds) and G-C pairs (3 hydrogen bonds).

The design and the synthesis of these probes are complicated by the degeneration of the genetic code: apart from the methionine (AUG) and the tryptophane (UGG) which necessitate a single codon, all the other amino acids are translated from 2 to 6 codons.

Until now, probes were obtained from a predetermined protein sequence by several strategies:

(a) Selecting in a sequence G in preference to A and T in preference to C. This gives to the hybridization either a stable pair, or a poor G-T match, which is called generally and in the following G-T "mismatch." This method has been applied with success to the synthesis of cDNA coding rat relaxin [P. Hudson et coll., Nature (1981) 291: 127], but is generalisable with difficulty by reason of its lack of sensitivity.

(b) Preparing all the possible sequences with the corresponding ambiguities [B. E. Noyes et coll., Proc. Natl. Acad. Sci., USA, (1979), 76: 1770 and M. Mevarech et coll., J. Biol. Chem., (1979) 254: 7472], which can necessitate an enormous amount of work for the synthesis.

(c) Synthesizing "mixed probes" with all the ambiguities on the same sequence. This technique has given good results for B-globin [R. B. Wallace et coll., Nucleic Acids Research (1981) 9: 879], for example, but represents for the organic chemist a "frustrating" side in view of the complexity of the mixture obtained and the number of trimers involved. This strategy does not always give satisfactory results because of the different reactivities of the various trimers involved at the level of each ambiguity. This leads to a lack of certainty as to the exact composition of the mixture obtained.

SUMMARY OF THE INVENTION

This invention overcomes at least in part, the drawbacks of the prior techniques by providing a probe which:

- can itself alone replace complex mixtures of sequences, and thus provide a considerable gain in time and money;
- has a well defined composition;
- has, with respect especially to the probes defined under (a) above, a better sensitivity in the detection after hybridization with complementary sequences and better stability of the hybrid thus formed (higher melting temperature);

and at the most, as will be seen below,

- are capable of being used with identification methods based on immunological or even immunoenzymatic reactions instead of radioactive detections, which are relatively insensitive and have well known drawbacks.

It is known that when a 2'-desoxy adenosine (A) is replaced by a 2-amino-2'-desoxyadenosine (A*) in a nucleotide sequence, this leads to a hybrid in which a pair of AT has three hydrogen bonds and which has a stability equivalent to that of a pair CG [R. C. Comtor and P. R. Schimmel, Biophysical Chemistry, W. H. Freeman, San Francisco (1980)].

Autocomplementary sequences (hexamers and octamers) comprising 2-amino 2'-desoxy adenosine groups have already been synthesized for the purpose of examining the stability and the conformation (in B or Z form) of DNA models in spectroscopic studies (circular dichroism) [B. L. Gaffney et coll., Nucleic Acids Research (1982), 10: 4351 and Tetrahedron (1984), 40: 3].

It has not yet been proposed, nor even suggested, to prepare oligonucleotide sequences including modified adenine groups so that they may be capable of forming three hydrogen bonds with the reactive groups of thymine and to use such sequences as probes to obtain the advantages of the probe of the invention as described above.

The probe according to the invention, which is constituted by an oligonucleotide fragment of predetermined by structure, is characterized in that at least a part of the adenine groups therein is replaced by modified adenine groups so that they may be capable of forming three hydrogen bonds with the reactive groups of thymine or of uracil. The adenine groups are advantageously modified by introduction of a group on the C-2 position of the pyrimidine ring, wherein the group can form a hydrogen bond with the oxygen atom fixed to the C-2 position of the thymine or of uracil.

It is more particularly an object of the invention to provide a probe constituted by an oligonucleotide fragment having a predetermined structure based upon the application envisaged, characterized in that at least a part of the adenine groups therein is replaced by adenine groups modified by the introduction, on the C-2 position of the pyrimidine ring, of a group which can form a hydrogen bond with the oxygen atom fixed to the C-2 position of thymine or of uracil.

In order that a relatively stable hydrogen bond of this type may be formed, it is convenient for the group introduced onto the adenine group to be as short as possible. Preferred groups of this type are —NH$_2$ —OH, and —SH groups. The —NH$_2$ group is particularly preferred.

According to a preferred embodiment, the invention relates to a probe constituted by a oligonucleotide fragment of a structure predetermined by the use envisaged, characterised in that at least a part of the adenine groups therein is replaced by adenine groups modified by the introduction, onto the C-2 position of the pyrimidine ring, or an —NH₂, —OH, or —SH group, preferably —NH₂, that is to say groups represented by the general formula

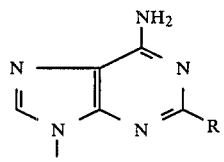

in which R represents —NH₂, —OH, or —SH. The probe according to the invention may, particularly advantageously, replace a "mixed probe" such as defined above, which is derived from a particular amino acid sequence and includes ambiguities.

Several specialized terms are used within this application. Among these is the term "degenerescence." This term is used to indicate the degeneracy of the genetic code and refers to the degenerated site, i.e. the site where the genetic code is said to be degenerate.

It has been discovered that this invention provides a probe giving a hybridization analogous to that of a mixed probe and confering a similar sensitivity in detection after hybridization with complementary sequences. More particularly, this invention provides a sequence derived from a particular amino acid sequence in which each degenerescence is replaced by one of the nucleotides of the degenerescence. In particular, T is replaced where a C/T degenerescence occurs, and G for a degenerescence G/A, and at least a part of the adenine groups is replaced by modified adenine groups as defined above. This discovery is surprising particularly to the extent that, as indicated above and as results clearly from the comparative tests described below, the choice of particular nucleotides in the case of degenerescence can lead to "mismatches." Mismatches can lead to a lack of sensitivity in detection or the impossibility of using the probe altogether.

According to a particular advantageous embodiment of the invention, a probe, such as defined above, is constituted by a sequence deduced from a particular amino acid sequence and in which each degenerescence is replaced by one of the nucleotides of the degenerescence, particularly T for a degenerescence C/T, and G for a degenerescence of G/A.

Although it is not indispensable, it is preferable in all cases, and in particular in the latter embodiment of the invention, to replace all the adenine groups of the oligonucleotide fragment by modified adenine groups such as defined above. This provides better sensitivity.

For the majority of uses, the probe according to the invention comprises less than 20 nucleotides. However, for certain uses it may be desirable to have a longer oligonucleotide fragment. Taking into account the absence of ambiguities, no technical limitation exists in principle to the preparation of longer fragments. Thus, it has been shown that it was possible to obtain sequences including more than 40 nucleotides.

The probe according to the invention may be prepared by any conventional process of preparing oligonucleotide fragments by replacing at least a part of the adenylic acid or desoxyadenylic acid groups, depending upon whether an RNA or DNA fragment is prepared, by adenylic or desoxyadenylic acid groups comprising a modified adenine group as defined above. Advantageously the preparation is carried out in the solid phase. A monomer, dimer, or trimer can be fixed, through its 3' end to the 5' end of the terminal 3' nucleotide of the desired sequence, fixed to a solid support. Successive fixations of monomers, dimers and/or trimers to the terminal 5' nucleotide of the chain obtained can then be carried out until the desired oligonucleotide fraction is produced. The product can be separated from the support. Such a preparation may be carried out according to the procedure described by B. L. Gaffney et coll. in the above-mentioned articles.

By "monomer," "dimer" or "trimer" are meant groups constituted, respectively, by 1, 2, or 3 nucleic acids, identical or different, which have to enter into the constitution of the probe.

It is self-evident that at the time of synthesis the reactive functions of these groups whose participation in the reaction is not desired, must be protected by means of protective groups, which can then be removed from the probe under non-degrading conditions. By way of non-limiting example, the preparation of monomers, dimers, and trimers bearing protective groups of this type may be carried out according to the procedures of K. Itakura et coll. in Nucleic Acids Research, (1980), 8: 5507.

Deblocking of the protective groups and purification of the oligonucleotides obtained may be carried out according to the teachings of S. Tran Dinh et coll., in Eur. J. Biochem. (1983), 133: 579–589 or of R. W. Barnett et coll., in Tetrahedron Lett. (1981), 22: 991–994.

For the preparation of the monomers, dimers, and trimers containing the modified adenine group, it is advantageous to use a nucleotide prepared by phosphorylation of the corresponding nucleotide, particularly in the series of DNAs:

when the adenine group must be modified on the C-2 position of the pyrimidine by a —NH₂ group, 5'-O-dimethoxytrityl N,N'diisobutyryl 2-amino 2'-desoxy adenosine prepared from 2'-desoxy guanosine, by analogy with the technique described by W. L. Sung in J.C.S. (Comm), 1089 (1981) for thymidine;

when the adenine group must be modified on the C-2 position of the pyrimidine by the —OH group, 5'-O-dimethoxytrityl, N-isobutyryl 2-hydroxy 2'-desoxy adenosine, which may be prepared also by analogy with the method of W. C. Sung, from the nucleoside derived from the corresponding xanthine; and when the adenine group must be modified on the C-2 position of the pyrimidine by an —SH group, 5'-O-dimethoxytrityl N-isobutyryl 2-mercapto 2'-desoxy adenosine, which may be prepared in the same manner as the corresponding 2-hydroxy derivative by replacing, by a known method, the —OH group by an —SH group.

In the RNA series, it is possible advantageously to use corresponding, modified adenosines.

The probe thus obtained is advantageously labelled by a technique customary in the field of biological analyses. This makes it possible to locate the probe after hybridization. Thus, the probe may be labelled radioactively, particularly with $^{32}P$ by means of $[\gamma\text{-}^{32}P]$ ATP in the presence of polynucleotide kinase as described in the following examples.

In addition, and this is one of the particular advantages of the probes of the invention, Applicants have established that the presence of modified adenine groups, modified particularly by —NH₂ groups at the C-2 position of the pyrimidine ring, favors the left configuration, called configuration Z, of the hybrids formed from sequences of this type, with respect to the usual B configuration, and that in the Z configuration, the modified adenine groups are more accessible to external reagents. This permits their location, particularly by specific antibodies of these bases, preferably monoclonal, whilst the B configuration only permits with difficulty, and even prevents, reagents from reaching the bases.

The invention also provides a probe, such as defined above, labelled radioactively, particularly by $^{32}$P.

The invention provides also oligonucleotides comprising protective groups and corresponding to the probes according to the invention, possibly bonded to solid supports.

The invention also comprises the oligonucleotides of the above-mentioned type comprising, in addition, modified adenine groups used according to the present invention and bases used customarily in oligonucleotide synthesis, other bases whose presence could be judged necessary, particularly X and/or Y modified bases, whose use forms the subject of FR patent application No. 84 13096, filed on Aug. 22, 1964, by the same Applicants and having as title "MIXED PROBE AND ITS USES, ITS PRECURSOR, THEIR PREPARATION AND DERIVATIVES COMPRISING A MODIFIED BASE FOR THIS PREPARATION."

On deblocking, these modified bases give a mixture, particularly equimolecular, according to the conditions of the reaction, or uracyl and of cytosine or of thymine and of 5'-methyl cytosine on the one hand, and guanine and 2-amino adenine on the other hand, according to the diagram:

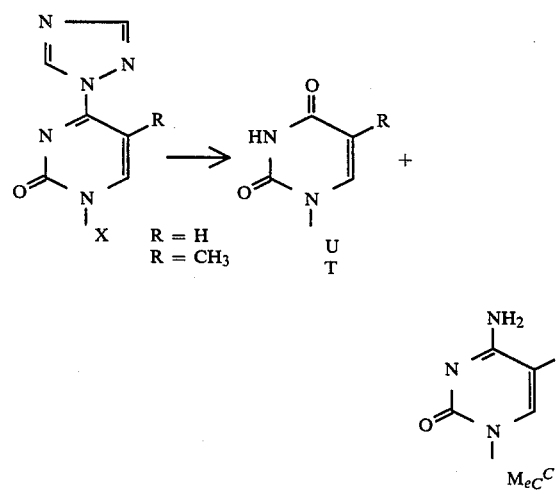

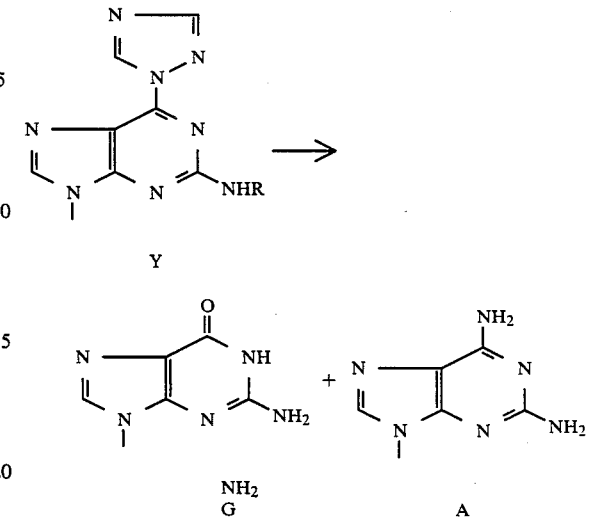

The invention also comprises the probes obtained on deblocking oligonucleotides containing X and/or Y bases.

The probe according to the invention can hence be used advantageously in techniques of analysis or of extraction, particularly RNA messengers or complementary DNAs, calling for the formation of immune complexes, particularly immuno-enzymatic reactions.

DETAILED DESCRIPTION OF PREFERRED EMBODIMENTS

There will be described below, by way of example, the application of the invention to the resolution of the problem posed by the isolation of the complementary DNA (cDNA) of antithrombin III.

The aminoacid sequence taken into consideration is $^{251}$Met—Met—Tyr—Gln—Glu—Gly$^{256}$ which corresponds to the sequence of ribonucleic acids

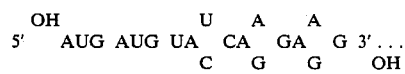

and to a cDNA which ca be written:

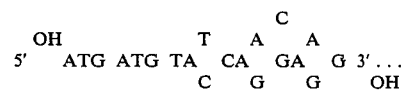

and which comprises 3 ambiguities.

Three probes were prepared for hybridization with the cDNA. The three probes were:
(1) a mixed probe comprising the three corresponding ambiguities (mixture of 8 hexadecamers):

3' TAC TAC AT$_G{}^A$ GT$_T{}^C$ CT$_T{}^C$ C 5'.

This probe was constructed from triplets in the solid phase by the techniques of R. B. Wallace et coll., described in Nucleic Acids Research (1981) 9: 879.
(2) The specific sequence

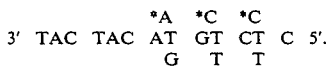

```
                 *A  *C  *C
       3'  TAC  TAC  AT  GT  CT  C  5'.
                     G   T
```

This sequence was prepared by means of dimers and trimers in the solid phase by the technique of H. Ito et coll, described in Nucleic Acids Research (1982), 10: 1755. In this sequence, when there was C/T degenerescence T was selected and when there was G/A degenerescence G was selected, for the reasons indicated above. In this selection process a "mismatch" was introduced on sixteen nucleotides (see below the actual structure of the cDNA).

(3) The specific sequence

```
              *          *        *
       3'  TAC  TAC  ATG  GTT  CTT  C  5'
                       =    =    =
``` according to the invention was prepared by means of monomers, dimers, and trimers in the solid phase by the above-indicated techniques with reference to this type of sequencing. In this sequence, the choice of degenerescence was the same as in sequece (2) and the adenosine A was replaced by 2-amino adenosine A*.

It was shown that sequence (3) forms with the cDNA a stabler hybrid than the sequence (2) (increase in the melting point of the hybrid) and gives a hybridization similar to that of the mixed probe (1). These three probes were labelled with $^{32}P$ and served for analyzing a "bank" containing cDNA of antithrombin III. The probes (1) and (3) permitted the isolation of the cDNA whose structure was proved by sequencing to be:

```
           OH
       5'      ATGATGTACCAGGAAG  3'
                      ‾   ‾        OH
```

In this formula, the nucleotides for which there was ambiguity, but no "mismatch" for the probes (2) and (3) are underlined by one line. Nucleotides for which there was ambiguity and a mismatch are underlined by two lines for the probes (2) and (3).

EXAMPLES

Preliminary example: preparation of the protected derivative of modified desoxyadenylic acid: 5-O-dimethoxytrityl O-(2-chloro-phenyl cyanoethyl) 3'-phosphate N,N' diisobutyryl 2-amino 2'-desoxy adenosine (DMT $A^{2-NHiBu}_{iBu}$ p)

Into a flask dried in the oven, 312 mg (4.52 mmoles) of sublimed triazole were dissolved in 4.5 ml of anhydrous dioxane. 372 mg (1.50 mmoles) of 2-chlorophenyl phosphorodichloridate and at 0° C., 445 μl of anhydrous triethylamine were added. A thick white precipitate was obtained which was left under stirring at ambient temperature for one hour and a half. This precipitate is filtered washed with dioxane directed on 620 mg (0.94 mM) of 5'-O-dimethoxytrityl N,N'diisobutyryl 2-amino 2'-desoxy adenosine (DMTA$^{2-NHiBu}_{iBu}$)

coevaporated twice with pyridine. It is left under stirring for one hour, then 160 μl of cyanoethanol and 233 μl of N-methyl imidazole added. Two hours later, the reaction was terminated, the product was evaporated to dryness, taken up again with dichloromethane, washed twice with 5% $NaH_2PO_4$ once with 5% $NaHCO_3$ and once with water. The organic phase was dried on sodium sulfate, filtered and evaporated to dryness. The foam obtained was precipitated with petroleum ether, then chromatographed on a silica column eluted with dichloromethane enriched progressively with methanol. 470 mg (yield 47%) of nucleotide DMT $A^{2-NHiBu}_{iBu}$ p where obtained.
[CCM: 0.70 $CH_2Cl_2$—MeOH (90-10)]

EXAMPLE 1

Synthesis of the mixed probe (1)

The mixed probe was "built" from 19 mg of resin T (resin bearing the nucleotide T and prepared according to the techniques of K. Itakura et coll., described in Nucleic Acids Research (1980), 8: 5473) with the following trimers prepared by the techniques of K. Itakura et coll., indicated above.

```
        CTT   CTT   GAT
         +     +     +     ACA   TCA   T  ~(
        CCT   CCT   GGT                     solid
         ↑     ↑     ↑     ↑     ↑          support
Yields  86%   83%   79%   50%
```

After the last coupling, the resin was treated with 500 μl of a molar mixture of pyridine aldoxime (PAO) in tetramethyl guanidine (TMG) supplemented with 500 ul of TMG overnight. After evaporation to dryness and heating with concentrated ammonia at 50° C. for three hours, the reaction medium was purified by chromatography on a Sephadex G-10 column (tradename of the Pharmacia company for a cross-linked polysaccharide column) followed by high performance liquid chromatography (HPLC) on a column in the reverse phase. The oligonucleotide mixture was then detritylated with 80% acetic acid for 5 min, evaporated to dryness (9 O.D.) (1 O.D.=one optical density unit, corresponding to 20–40 μg of sequence) and purified by preparative electrophoresis on acrylamide gel.

EXAMPLE 2

Synthesis of the sequence (2)

In the same way, the sequence (2) was synthesized in the solid phase from 20 mg of resin T with triisopropylbenzene sulfonyl nitro-triazole (TPSNT) as coupling agent

```
        CTT   CTT   GGT   AC    AT    CA   T  ~(
         ↑     ↑     ↑    ↑     ↑     ↑
Yield         61%   82%   74%   78%   96%
```

The sequence was purified as described previously with respect to Example 1 (6.6 O.D.).

EXAMPLE 3

Synthesis of the sequence (3) according to the invention (with A*)

The sequence containing A* was synthesized from 30 mg of resin T

```
CTT  CTT   GGT    A*   C   A*    TC   A*   T ~(
              ↑    ↑   ↑   ↑         ↑    ↑
Yield  63%   98% ≦99% 77% ≦99%      72% ≦99%
```

The deblocking comprises an additional step consisting of treatment with 1.87 ml of ethylene diamine for 76 hours after heating with concentrated ammonia. After purification by HPLC and electrophoresis, 2 O.D. of the oligonucleotide were obtained.

EXAMPLE 4

Labelling of the probes (1), (2) and (3) with $^{32}P$

50 μCi of [γ-$^{32}$P]ATP on 100 pmoles of the probe in a volume of 4 μl of mix and 0.5 μl of polynucleotide kinase [activity 5–20 10$^3$ units ml, Boehringer Mannheim] was added. It was left for one half hour at 37° C. [T. Maniatis et coll., Molecular Cloning, Cold Spring Harbor Lab. (1982)]. The reaction was stopped by the addition of 1.3 ul of buffer with bromophenol blue 100 mM of EDTA, 50% glycerol. The labelled product was purified on gel (0.4×30×40 cm) containing 19 g of bisacrylamide, 19 g of acrylamide and 10 ml of 1M tris borate for a total volume of 100 ml.

The electrophoresis with programming: 2000 V, 43 W, 40 mA, was stopped when the bromophenol blue reached one third of the length of the plate. The radioactive strip was cut up and extracted overnight in 2 ml of water.

EXAMPLE 5

Hybridization

Three colonies containing complete cDNA of AT III and 3 colonies containing a cDNA not related to the AT III were subcultured in 3 examples on dishes of complete medium with 50 μg/ml of ampicillin. The colonies were transferred to three filters of Whatman 541 type, amplified for 20 hours on dishes containing 250 μg/ml of chloramphenicol and prepared for hybridization by the technique described by J. P. Gergen et coll., in Nucleic Acids Research (1979), 7: 2115. The filters were hybridized two hours at 42° C. in 6 NET (1 NET=0.15M NaCl 0.015M tris HCl pH=7.5. 0.001M EDTA 0.5% Monidet P40 (tradename for a detergent), 100 μg/ml of yeast tRNA and 100 μg/ml of sonicated salmon sperm DNA (technique of T. Maniatis et coll., in the article mentioned above). The hybridization was carried out at 42° C. for 20 hours in the same solution in the presence of 10$^6$ cpm of oligonucleotide labelled at the 5' position with [γ-$^{32}$P]ATP, each filter having been hybridized with one of the three probes. The filters were washed 4 times for 15 minutes at 40° C. in 6 SSC (1 SSC=0.15M NaCl, 0.015M sodium citrate pH=7.2), 0.1% of sodium dodecyl sulfate (SDS). The filters were subjected to autoradiography.

The hybridization was visible on the mixed probe (1) (1 sequence in 8 was complementary to the cDNA) and in the specific sequence (3) including 3 A* (1 "mismatch" and 9/16 pairs of type GC), whilst the sequence (2) (1 "mismatch" and 6/16 pairs of type GC) did not hybridize. The difference of melting point of the hybrids with the probes (2) and (3) is of the order of 7° C., the hybrid formed with the probe (3) having the highest melting point.

The "mix" is a mixture of:
tris (hydroxymethyl) aminomethane (500 mM, pH 8);
MgCl$_2$ (100 mM); and
dithiotreitol (50 mM).

We claim:

1. A method of detecting a DNA segment which encodes for a peptide of known amino acid sequence, and wherein said DNA segment has more than one possible nucleotide sequence because of the degeneracy of the genetic code, wherein the method comprises:
   providing a DNA probe comprising an oligonucleotide containing adenosine groups, at least a portion of which comprise a substituted adenine group of the formula:

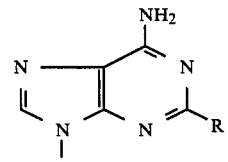

in which R is an —NH$_2$, —OH, or —SH moiety;
contacting said probe with said DNA segments under conditions to form a hybrid duplex molecule in which said adenine in said probe pairs with thymine in said DNA segment and forms three hydrogen bonds with reactive groups of said thymine; and
detecting said hybrid duplex molecule;
wherein the DNA probe is substantially complementary to the DNA segment, and wherein said DNA segment, because of the degeneracy of the genetic code, has one or more C/T degeneracies and/or one or more G/A degeneracies, and said probe has a G at the complementary position to said C/T degeneracies and a T at the complementary position to said G/A degeneracies.

2. Method as claimed in claim 1, wherein the oligonucleotide contains up to about 40 nucleotides.

3. Method as claimed in claim 1, wherein the oligonucleotide contains less than 20 nucleotides.

4. Method as claimed in claim 1, wherein R is —NH$_2$.

5. Method as claimed in claim 1, wherein R is —OH.

6. Method as claimed in claim 1, wherein R is —SH.

7. Method as claimed in claim 1, wherein all of the adenine groups in said probe have said formula.

8. Method as claimed in claim 1, wherein said probe is labeled.

9. Method as claimed in claim 8, wherein a radioactive label is bound to said probe and said label is detected after formation of said hybrid.

10. Method as claimed in claim 9, wherein said radioactive label is $^{32}$P.

11. Method as claimed in claim 1, wherein said oligonucleotide is bonded to a solid support.

12. Method as claimed in claim 4, wherein all of the adenine groups in said probe have said formula.

13. Method as claimed in claim 5, wherein all of the adenine groups in said probe have said formula.

14. Method as claimed in claim 6, wherein all of the adenine groups in said probe have said formula.

* * * * *